United States Patent [19]

Gauthier-Lafaye et al.

[11] Patent Number: 4,997,978

[45] Date of Patent: Mar. 5, 1991

[54] PREPARATION OF ALKYL CARBOXYLATES BY HYDROCARBONYLATION

[75] Inventors: Jean Gauthier-Lafaye, Lyon; Robert Perron, Charly, both of France

[73] Assignee: Rhone-Poulenc Industries, Paris, France

[21] Appl. No.: 261,635

[22] Filed: Oct. 24, 1988

Related U.S. Application Data

[63] Continuation of Ser. No. 100,462, Sep. 24, 1987, abandoned, which is a continuation of Ser. No. 856,343, Apr. 28, 1986, abandoned, which is a continuation of Ser. No. 408,040, Aug. 13, 1982, abandoned, which is a continuation of Ser. No. 216,913, Dec. 16, 1980, abandoned.

[30] Foreign Application Priority Data

Dec. 21, 1979 [FR] France ..................... 79 32137

[51] Int. Cl.$^5$ ............... C07C 67/36; C07C 69/003
[52] U.S. Cl. ................ 560/265; 260/410.9 R;
560/1; 560/103; 560/105; 560/106; 560/122;
560/123; 560/124; 560/254; 568/484; 568/876;
568/885
[58] Field of Search ............ 560/265, 232, 105, 106,
560/103, 122, 123, 124, 114, 1; 260/410.9 R

[56] References Cited

U.S. PATENT DOCUMENTS 3,285,948  11/1966  Butter ................................. 560/265
4,189,441   2/1980  Braca et al. ....................... 560/232

Primary Examiner—Vivian Garner
Attorney, Agent, or Firm—Burns, Doane, Swecker & Mathis

[57] ABSTRACT

Alkyl carboxylates of the formula:

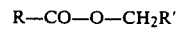

are prepared by hydrocarbonylating a compound of the formula:

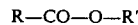

in the simultaneous presence, in the reaction medium, of cobalt, ruthenium, an alkyl iodide and an ionic iodide, the atomic ratio Co/Ru being less than or equal to 1, and the total amount of iodine-containing promoters present in the medium being such that I/Ru is greater than or equal to 5.

18 Claims, No Drawings

PREPARATION OF ALKYL CARBOXYLATES BY HYDROCARBONYLATION

This application is a continuation of application Ser. No. 100,462, filed Sept. 24, 1987, which is a continuation of Ser. No. 856,343, filed Apr. 28, 1986, which is a continuation of application Ser. No. 408,040, filed Aug. 13, 1982, which is a continuation of application Ser. No. 216,913, filed Dec. 16, 1980, all now abandoned.

BACKGROUND OF THE INVENTION

1. Field of the Invention

The present invention relates to the improved preparation of the alkyl carboxylates, notably the alkyl acetates, by reacting a gaseous mixture comprising carbon monoxide and hydrogen with the next lower homolog of the desired alkyl carboxylate. By "next lower homolog" as used herein, there is intended the corresponding carboxylate, in the alcohol moiety of which the alkyl radical contains one less carbon atom than the ultimately desired compound.

The process according to the present invention is more especially adapted for the preparation of ethyl acetate from methyl acetate.

2. Description of the Prior Art

Certain authors (compare *Journal of the American Chemical Society,* 100: 19, 1978, pages 6,238–6,239) have reported that it is possible, in particular, to prepare ethyl acetate by the hydrocarbonylation of methyl acetate in the simultaneous presence of ruthenium, an iodine-containing promoter and a proton donor (which is either HI, introduced at the beginning of the reaction or formed in situ from $CH_3I$, or a carboxylic acid).

However, the industrial-scale development of a technique of this type, the fundamental value of which cannot be disputed, is exceedingly compromised by the low activity of the catalyst system employed.

Recently, it too has been proposed (compare published French Patent Application No. 78/20,843) to carry out this reaction in the presence of a cobalt salt and iodine. However, the high pressures which are required for the catalyst system to develop an acceptable activity are such that it too is hardly possible to envisage industrial development of a process of this type.

Thus, a clear and present need exists in this art for a process for the preparation of the alkyl carboxylates from their next lower homologs, which process would make it possible to operate under low pressure, with an industrially satisfactory reaction rate, but without a consequent loss in terms of selectivity with respect to the ultimately desired ester.

SUMMARY OF THE INVENTION

Accordingly, a major object of the present invention is the provision of an improved process for the hydrocarbonylation of the alkyl esters, devoid of those disadvantages and drawbacks above outlined, and which improved process features the preparation of alkyl carboxylates by reacting a gaseous mixture containing carbon monoxide and hydrogen with the next lower homologs of the desired alkyl carboxylates, characterized in that the reaction is carried out in the simultaneous presence, in the reaction medium, of a catalytically effective amount of ruthenium, cobalt, the atomic ratio Co/Ru being less than or equal to 1, at least one alkyl iodide and at least one inorganic or organic ionic iodide in which the cation comprises alkali metal cations, alkaline earth metal cations, or quaternary ammonium or phosphonium cations, the total amount of iodine-containing promoters present in the reaction medium being such that the atomic ratio I/Ru is greater than or equal to 5.

DETAILED DESCRIPTION OF THE INVENTION

More particularly according to this invention, the process featured hereby can be represented by the following reaction:

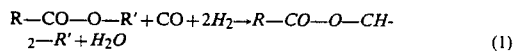

$$R-CO-O-R' + CO + 2H_2 \rightarrow R-CO-O-CH_2-R' + H_2O \qquad (1)$$

in which R represents a linear or branched chain alkyl radical having from 1 to 16 carbon atoms, a cycloalkyl radical having from 3 to 6 carbon atoms, a phenyl radical ($C_6H_5-$), a radical $C_6H_5-C_xH_{2x}-$ or a radical $C_xH_{2x+1}-C_6H_4-$, x being an integer between 1 and 6 inclusive, and R' represents a linear or branched chain alkyl radical having from 1 to 5 carbon atoms, or a radical $C_6H_5-C_xH_{2x}-$ having the above meaning, it also being possible for R and R' to be identical.

R' is preferably a methyl radical.

R is advantageously an alkyl radical having from 1 to 4 carbon atoms, such as methyl, ethyl, n-propyl, isopropyl, n-butyl, secondary butyl, isobutyl or tert-butyl.

Indeed, it too has totally unexpectedly been determined that the addition of a small amount of cobalt to a catalyst system containing ruthenium gives rise to a considerable increase in the activity of said system, even in a pressure range within which cobalt, used in isolation, exhibits virtually no activity.

Thus, it is apparent that one of the essential constituents of the catalyst system according to the present invention is ruthenium. But the precise form in which the ruthenium is used in the reaction is not of fundamental importance. Ruthenium carbonyls, such as $Ru_3(CO)_{12}$, $[Ru(CO)_3Br_2]_2$, and $Ru(CO)_4I_2$, and more generally any ruthenium compound which is capable of, under the reaction conditions, effecting the formation of ruthenium carbonyls in situ, are particularly suitable for carrying out the present process. In this respect, ruthenium metal in a finely divided form, ruthenium tribromide, ruthenium triiodide, ruthenium carboxylates (in particular ruthenium acetate) and ruthenium acetylacetone are especially noteworthy.

The amount of ruthenium to be used is not critical. As the proportion of ruthenium in the reaction medium has a positive influence on the reaction rate, it will be determined in accordance with the rate which it will be judged appropriate to attain.

In general terms, an amount of between 0.5 and 100 milligram atoms of ruthenium per liter of reaction medium (mg atoms/liter) affords satisfactory results. The reaction is preferably carried out with a proportion of ruthenium of between 1 and 50 atoms/liter of reaction medium.

The second essential constituent of the catalyst system according to the invention is cobalt. Any source of cobalt which is capable of reacting with carbon monoxide in the reaction medium to provide cobalt carbonyl complexes can be used within the scope of the present process.

Examples of typical sources of cobalt are finely divided cobalt metal, inorganic salts, such as cobalt nitrate or carbonate, and organic salts, in particular carboxylates. Cobalt carbonyls or hydrocarbonyls can also be used.

Among the cobalt derivatives which are suitable for carrying out the process according to the invention, there are noted cobalt formate, cobalt acetate, cobalt halides, and more particularly cobalt iodide, and dicobalt octacarbonyl.

A notable characteristic of the present process is in the fact that the amount of cobalt used in the reaction is such that the atomic ratio Co/Ru is always less than or equal to 1. In general, the ratio is between 0.01 and 1, preferably between 0.02 and 0.50 and most preferably between 0.05 and 0.25.

The process according to the present invention also requires the presence, in the reaction medium, of at least one alkyl iodide, which can be represented by the formula R″-I, in which R″ has the meaning given above for R′, it being possible for R″ and R′ to be identical or different.

Of course, the alkyl iodide, which can be introduced at the start of the reaction, is capable of being formed in situ under the reaction conditions, in particular from iodine, hydriodic acid, an acyl iodide (R″-CO-I), cobalt iodide and/or ruthenium iodide.

In other words, all or part of the alkyl iodide which must be present in the reaction medium in order to carry out the present process can be formed from its precursors defined above.

It will also be apparent that, if the iodine derivative is selected from among cobalt compounds or ruthenium compounds, it can be considered not only as a precursor of the alkyl iodide, but also as a precursor of the metal catalyst (or catalysts).

Within the scope of the present invention, lower alkyl iodides having from 1 to 4 carbon atoms constitute a preferred class of alkyl iodides. Methyl and ethyl iodides are particularly advantageous for carrying out the process according to the invention.

To carry out the subject process satisfactorily, an alkyl iodide concentration of at least 5 millimols per liter of reaction medium (mmols/liter) is typically required. However, there is no advantage in exceeding a concentration of 500 mmols/liter, the risks of corrosion of the equipment being liable to increase because of the formation of water, as shown by reaction (1) above.

The process according to the present invention also requires the presence, in the reaction medium, of at least one inorganic or organic ionic iodide, the cationic moiety of which being selected from the group comprising alkali metal cations, alkaline earth metal cations and the quaternary ammonium or phosphonium cations illustrated by the formulae I to III below:

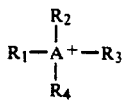

in which A represents a nitrogen or phosphorus atom and $R_1$, $R_2$, $R_3$ and $R_4$, which can be identical or different, represent hydrogen or, preferably, organic radicals with the free valencies thereof borne by carbon atoms, it being possible, if appropriate, for any two of these various radicals together to form a single divalent radical.

More specifically, $R_1$, $R_2$, $R_3$ and $R_4$ can represent linear or branched chain alkyl radicals or monocyclic cycloalkyl, aralkyl (for example, benzyl) or aryl radicals having at most 16 carbon atoms, which can be substituted, if appropriate, by 1 to 3 alkyl radicals having from 1 to 4 carbon atoms; it also being possible, if appropriate, for two of the radicals $R_1$ to $R_4$ together to form a single divalent alkylene or alkenylene radical containing 3 to 6 carbon atoms (for example, a tetramethylene or hexamethylene radical) and, if appropriate, 1 or 2 ethylenic double bonds; and it too being possible for the said radical to carry 1 to 3 alkyl substituents having from 1 to 4 carbon atoms.

in which $R_5$, $R_6$, $R_7$ and $R_8$, which are identical or different, represent alkyl radicals having from 1 to 4 carbon atoms, it also being possible for one of the radicals $R_7$ or $R_8$ to represent hydrogen, and it also being possible, if appropriate, for $R_7$ and $R_8$ together to form a single divalent alkylene radical containing from 3 to 6 carbon atoms, for example, tetramethylene or hexamethylene; $R_6$ and $R_7$ or $R_8$ can together form a single divalent alkylene or alkenylene radical containing 4 carbon atoms and, if appropriate, 1 or 2 ethylenic double bonds, the nitrogen atom in that case being included in a heterocyclic ring to form, for example, a pyridinium cation.

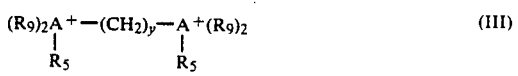

in which R5 and A+ are as defined above, R9, which can be identical to R5, represents an alkyl radical having from 1 to 4 carbon atoms, or a phenyl radical, and y is an integer between 1 and 10, inclusive, and preferably between 1 and 6, inclusive. The following iodides are exemplary of quaternary ammonium iodides which are suitable for carrying out the subject process: tetramethylammonium, triethylmethylammonium, tributylmethylammonium, trimethyl-(n-propyl)-ammonium, tetraethylammonium, tetrabutylammonium, dodecyltrimethylammonium, benzyltrimethylammonium, benzyldimethylpropylammonium, benzyldimethyloctylammonium, dimethyldiphenylammonium, methyltriphenylammonium, N,N-dimethyl-trimethyleneammonium, N,N-diethyltrimethyleneammonium, N,N-dimethyl-tetramethyleneammonium, N,N-diethyl-tetramethyleneammonium, N-methylpyridinium, N-ethylpyridium and N-methylpicolinium.

The following iodides are exemplary of quaternary phosphonium iodides which are also suitable for carrying out the process according to the invention: tetramethylphosphonium, ethyltrimethylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri-(isopropyl)- phosphonium, methyl-tri-(n-propyl)phosphonium, methyl-tri-(n-butyl)-phosphonium, methyl-tris-(2-methylpropyl)-phosphonium, methyltricyclohexylphosphonium, methyltriphenylphosphonium, methyltribenzylphosphonium, methyltris-(4-methylphenyl)-phosphonium, methyltrixylylphosphonium, diethylmethylphenylphosphonium, dibenzylmethylphenylphosphonium, ethyltriphenylphosphonium, tetraethylphosphonium, ethyl-tri-(n-propyl)-phosphonium, triethylpentylphosphonium, ethyltriphenylphosphonium, n-butyl-tri-(n-propyl)-phosphonium, butyltriphenylphosphonium, benzyltriphenylphosphonium, (β-phenylethyl)-dimethylphenylphosphonium, tetraphenylphosphonium and triphenyl-(4-methylphenyl)-phosphonium.

The precise nature of the quaternary ammonium or phosphonium cation is not of fundamental importance within the scope of the subject process. The choice from among these compounds is governed more by practical considerations, such as solubility in the reaction medium, the availability thereof and the convenience of use.

In this respect, the quaternary ammonium or phosphonium iodides represented either by the formula (I) in which any one of the radicals $R_1$ to $R_4$ is selected from among linear alkyl radicals having from 1 to 4 carbon atoms, or by the formulae (II) or (III) in which $R_5$ (or $R_6$) is also an alkyl radical having from 1 to 4 carbon atoms, are particularly suitable.

Moreover, the preferred ammonium iodides are those in which the cations correspond to the formula (I) in which all the radicals $R_1$ to $R_4$ are selected from among linear alkyl radicals having from 1 to 4 carbon atoms, and in which at least three of them are identical.

Likewise, the preferred quaternary phosphonium iodides are those in which the cations correspond to the formula (I) in which any one of the radicals $R_1$ to $R_4$ represents a linear alkyl radical having from 1 to 4 carbon atoms, the other three radicals being identical and selected from among phenyl, tolyl and xylyl radicals.

The alkali metal iodides, in particular the iodides of lithium, potassium and sodium, constitute a preferred class of ionic iodides within the scope of the present invention. The quaternary phosphonium iodides, and more particularly those in which the cations correspond to the formula (I) above, in which one of the radicals $R_1$ to $R_4$ is an alkyl radical having from 1 to 4 carbon atoms, the other three radicals being identical and selected from among phenyl, tolyl and xylyl radicals, constitute another class of ionic iodides which are particularly effective for carrying out the present invention.

Although the amount of ionic iodide which must be present in the reaction medium can vary within wide limits, it is generally such that the ratio $I^-/Ru$ is between 1 and 100; this ratio is advantageously fixed at a value situated in the range of 2 to 50.

According to an essential characteristic of the present process, the total amount of iodine-containing promoters present in the reaction medium is such that the atomic ratio I/Ru is greater than or equal to 5; there is no point in exceeding a value of 100. Advantageously, the total amount of iodine-containing promoters present in the reaction medium is such that the atomic ratio I/Ru is between 10 and 50.

It too has unexpectedly been found quite surprisingly, that the addition of an alkali metal co-catalyst or alkaline earth metal co-catalyst, to the reaction medium containing cobalt, ruthenium, the atomic ratio Co/Ru being less than or equal to 1, an alkyl iodide and an ionic iodide defined above, has a considerable influence on the reaction selectivity with respect to the desired ester. For this purpose, it is possible to use inorganic or organic salts of sodium, potassium, lithium, cesium, rubidium, calcium or magnesium, and more particularly the oxides, the hydroxides, the carbonates, the nitrates, the alcoholates ($R'''—O^-$) and the carboxylates ($R'''—CO—O^-$) of the above-mentioned metals, $R'''$ having the meaning given for R, and it being possible for $R'''$ and R to be identical or different. Carboxylates, and more particularly the acetates, are convenient to use and can be recommended in this respect. The acetates of lithium, sodium, potassium and magnesium are particularly suitable for carrying out the subject process.

Although the use of this co-catalyst constitutes one advantageous embodiment of the present invention, it is in no event obligatory or critical.

An amount of co-catalyst on the order of 1 to 500 gram atoms of alkali metal or alkaline earth metal per gram atom of ruthenium present in the reaction medium provides satisfactory results, although smaller or larger amounts can be used. Good results are obtained if the atomic ratio of the alkali metal or alkaline earth metal to the ruthenium is between 2 and 250.

Good results are obtained, in particular, if methyl iodide, an alkali metal iodide and a magnesium salt are introduced at the outset, or alternatively if methyl iodide, a quaternary phosphonium iodide and a lithium salt are introduced at the outset It has also been found that, if an alkyl iodide and/or one of its precursors defined above are introduced at the outset in an amount such that the ratio I/Ru is greater than or equal to 5, the alkali metal or alkaline earth metal iodides can be re placed in the initial charge, by any one of the corresponding metal salts mentioned above. Within the scope of this modified embodiment, the amount of salts introduced is such that the molar ratio of the alkali metal or alkaline earth metal to the alkyl iodide is between 0.1 and 10 inclusive. This ratio is advantageously fixed at a value between 0.25 and 5 inclusive. Good results are obtained if methyl iodide is introduced at the beginning in an amount such that the ratio $CH_3I/Ru$ is greater than or equal to 5, together with lithium acetate, sodium acetate, potassium acetate or magnesium acetate.

The process according to the present invention is preferably carried out in the liquid phase. It is possible to use solvents or diluents, in particular a carboxylic acid of the formula $R'''—COOH$, in which $R'''$ is as above defined for R, it being possible for $R'''$ and R to be identical or different, and the carboxylic acid not necessarily corresponding to the alkali metal carboxylates (or alkaline earth metal carboxylates) considered above. However, the presence of a solvent of this type only constitutes an advantageous modified embodiment of the present process.

It will be noted that water is produced in reaction (1) described above. It has also been found that the presence of water does not detract from satisfactorily carrying out the process, and that, to the contrary, the presence of water introduced at the very outset tends to favor the reaction in certain cases. It is therefore possible to use reactants of technical grade, which contain up to about 10% by weight of water, if appropriate.

According to the present invention, the catalyst system and the starting material, defined above, and also solvents or diluents, if appropriate, are introduced into a pressure resistant reactor made of a suitable material, under an atmosphere of hydrogen and carbon monoxide. The molar ratio $H_2/CO$, which is established by the stoichiometry of the equation given above, can nevertheless vary within wide limits and is typically between 1/5 and 5/1 and preferably between 1/1 and 3/1. Of course, the mixture of gases can contain impurities, in particular carbon dioxide, oxygen, methane and/or nitrogen.

The reactor is then heated to the reaction temperature. A temperature which is typically above 150° C. is recommended. This temperature is more particularly between 175° and 250° C.; good results are obtained within the temperature range between 190° C. and 230° C.

The reaction is carried out under pressure. The total pressure is generally more than 50 bars and can be as high as 600 bars. Nevertheless, the new catalyst system which is the focus of the present invention makes it possible to obtain appreciable results within a pressure range between 150 and 350 bars.

An additional advantage of the present process is in the fact that the low proportion of liquid by-products formed consists essentially of products which can be recycled.

Upon completion of the reaction, the final products obtained can easily be separated, for example by fractional distillation of the resulting mixture; the by-products, in particular the carboxylic acid formed, can be recycled into the reaction.

In order to further illustrate the present invention and the advantages thereof, the following specific examples are given, it being understood that same are intended only as illustrative and in nowise limitative.

In the examples to follow, the following abbreviations are used:
AcOEt denotes ethyl acetate
MeOH denotes methanol
AcH denotes acetaldehyde
EtOH denotes ethanol
AcOH denotes acetic acid
V: number of mols of carbon monoxide absorbed per second and per mol of cobalt used in the reaction.

furnace. The pressure in the autoclave was then 220 bars and same was maintained between 230 and 260 bars by successively introducing additional amounts of the initial mixture of $H_2/CO$.

After a reaction time of 40 minutes at the temperature indicated, the heating and the shaking were stopped; the autoclave was cooled and degassed. The resulting reaction mixture was analyzed by gas chromatography (after dilution in a 56/44 mixture of water and 1,2-dimethoxyethane and acidification with 36 N sulphuric acid). It contained 24.25 g of ethyl acetate, together with 1.85 g of methanol, 0.45 g of acetaldehyde, 1.95 g of ethanol and 35.45 g of acetic acid.

The productivities of the reaction with respect to ethyl acetate were therefore as follows:
25 365 grams per hour and per liter (g/hour × liter),
270 grams per hour and per gram of ruthenium (g/hour × g of Co).

Control experiments (a) to (e)

A series of experiments was carried out in accordance with the procedure described in the aforesaid Example 1. These experiments do not fall within the scope of the process according to the invention.

In control experiment (a), the dicobalt octacarbonyl was omitted.

In control experiment (b), the triruthenium dodecacarbonyl was omitted.

In control experiment (c), the dicobalt octacarbonyl was replaced by an equivalent amount of iron pentacarbonyl (0.21 mg atom of iron).

In control experiment (d), the triruthenium dodeca carbonyl was replaced by an equivalent amount of iron pentacarbonyl (1.31 mg atoms of iron).

In control experiment (e), the methyltriphenylphosphoniu iodide was omitted; the resulting ratio I/Ru is only 2.7.

The particular conditions and also the results obtained are reported in Table I below, in which certain condition and the results obtained in Example 1 have been repeated.

TABLE I

| REFERENCE | CATALYST | | REACTION TIME | AcOEt (g) | MeOH (g) | AcH (g) | EtOH (g) | AcOH (g) | V |
|---|---|---|---|---|---|---|---|---|---|
| 1 | Ru | Co | 40 minutes | 24.25 | 1.85 | 0.45 | 1.95 | 35.45 | 0.77 |
| a | Ru | — | 1 hour 15 minutes | 6.30 | 1.5 | — | — | 30.70 | ND |
| b | — | Co | 1 hour 15 minutes | 0.9 | 1.2 | 2.75 | — | 29.70 | 0.11 |
| c | Ru | Fe | 1 hour 15 minutes | 8.60 | 0.4 | — | — | 24.10 | ND |
| d | Fe | Co | 1 hour 15 minutes | 0 | — | 2.45 | — | 30.35 | 0.12 |
| e | Ru | Co | 1 hour 15 minutes | 6.30 | 0.65 | — | 0.25 | 22.80 | 0.08 |

This table clearly evidences the particular nature of the association of a small amount of cobalt with ruthenium. Furthermore, control experiment (e) demonstrates the importance of the amount of iodine -containing promoters present in the reaction medium.
ND = non-determinable.

EXAMPLE 1

The following compounds were introduced into a Z-8 CNDT 17-12 (AFNOR Standard Specification) stainless steel autoclave of 250 ml capacity: 80 ml (1,002 mmols) of methyl acetate, 20 ml (350 mmols) of acetic acid, 510 mg (3.54 mmols) of methyl iodide, 4.85 g (12 mmols) of methyltriphenylphosphonium iodide, 36.8 mg of dicobalt octacarbonyl (0.22 mg atom of Co), 279.2 mg of triruthenium dodecacarbonyl (1.31 mg atoms of Ru) and 50 mmols of lithium acetate. After closing the autoclave, a pressure of 140 bars was established using a mixture of $H_2/CO = 2/1$ (molar ratio). Shaking by means of a reciprocating system was begun and the autoclave was heated to 215° C., over the course of about 25 minutes, by means of an annular EXAMPLES 2 to 4

Using the autoclave and the procedure described above, a series of experiments was carried out, the following being introduced in each experiment: 0.215 mg atom of cobalt in the form of dicobalt octacarbonyl, 1.31 mg atoms of ruthenium in the form of triruthenium dodecacarbonyl, and 12 mmols of sodium iodide (Examples 3 and 4) or 12 mmols of methyltriphenylphosphonium iodide (Example 2).

The common operating conditions were as follows:
$H_2/CO$ : 2/1 (molar ratio)
Temperature : 215° C.

Total pressure at the temperature indicated : 260 bars
Duration of the experiment at the temperature indicated : 1 hour, 15 minutes.

The particular conditions and also the results obtained are reported in Table II below.

TABLE II

| Example No. | CHARGE AcOMe (mmols) | AcOH (mmols) | $H_2O$ (mmols) | $CH_3I$ (mmols) | AcOEt (g) | V |
|---|---|---|---|---|---|---|
| 2 | 1,253 | 0 | 0 | 3.54 | 9.3 | 0.37 |
| 3 | 1,000 | 350 | " | " | 18.0 | 0.48 |
| 4 | " | 350 | 170 | 3.62 | 15.9 | 0.27 |

EXAMPLES 5 to 11

Using the autoclave and the procedure described above, a series of experiments was carried out, the following being introduced in each experiment: 1,000 mmols of methyl acetate, 350 mmols of acetic acid, 12 mmols of sodium iodide, 1.31 mg atoms of ruthenium in the form of triruthenium dodecacarbonyl, and methyl iodide and dicobalt octacarbonyl, unless otherwise stated The common operating conditions were as follows:
$H_2/CO$ 2/1 (molar ratio)
Temperature : 215° C.
Total pressure at the temperature indicated : 260 bars (unless otherwise indicated).

The particular conditions and also the results obtained are reported in Table III below, in which $Mg(OAc)_2$ denotes magnesium acetate tetrahydrate.
N.B. : the amount of water indicated in Table III does not include the water of hydration which may be introduced with the alkali metal salt.

TABLE III

| Example No. | $H_2O$ mmols | $CH_3I$ mmols | Co mg atoms | CO-CATALYST nature | mmols | Reaction time | AcOEt g | g/hour × liter | V | S |
|---|---|---|---|---|---|---|---|---|---|---|
| 5* | 170 | 3.66 | 0.22 | LiOAc | 50 | 2 hours 20 minutes | 7.75 | 35 | 0.08 | 63 |
| 6 | 67 | ** | 1.08 | $Mg(OAc)_2$ | 25 | 40 minutes | 5.90 | 90 | 0.03 | 84 |
| 7 | " | 7.04 | 0.12 | " | " | 40 minutes | 7.95 | 120 | 0.43 | 72 |
| 8 | " | 7.02 | 0.22 | " | " | 40 minutes | 10.90 | 160 | 0.35 | 67 |
| 9 | " | 3.54 | " | " | " | 40 minutes | 14.80 | 220 | 0.41 | 82 |
| 10 | 170 | 3.52 | " | LiOAc | 5 | 1 hour 15 minutes | 20.65 | 165 | 0.30 | 81 |
| 11 | " | 3.62 | 0.21 | LiOAc | 50 | 1 hour 15 minutes | 17.95 | 145 | 0.32 | 68 |

*Example carried out at 170° C. with a molar ratio $H_2/CO:1$, under 230 bars.
**Example carried out with 474 mmols of $I_2$ and 1.08 mg atoms of Co in the form of $CoI_2$ and under 160 bars.

EXAMPLES 12 to 16

Using the autoclave and the procedure described above, a series of experiments was carried out, the following being introduced in each experiment: 0.22 mg atom of cobalt in the form of dicobalt octacarbonyl, ruthenium in the form of triruthenium dodecacarbonyl, 3.55 mmols of methyl iodide, 12 mmols of methyltri-phenylphosphonium iodide, 1,000 mmols of methyl acetate and 350 mmols of acetic acid (unless otherwise indicated).

The common operating conditions were as follows:
$H_2/CO$ : 2/1 (molar ratio)
Temperature : 215° C.
Total pressure at the temperature indicated : 260 bars
Duration of the experiment at the temperature indicated : in principle, 1 hour, 15 minutes.

The particular conditions and also the results obtained are reported in Table IV below.

N.B.: In Tables III and IV, S denotes the molar ratio:

$$\frac{\text{(AcOEt) formed}}{\text{(AcOEt + EtOH + AcOH + AcH) formed}} \times 100$$

TABLE IV

| Example No. | Ru mg atoms | CO-CATALYST nature | mmols | AcOEt g | g/hour × liter | V | S |
|---|---|---|---|---|---|---|---|
| 12(*) | 1.31 | LiOAc | 50 | 21.8 | 175 | 0.51 | 51 |
| 13(**) | 1.31 | " | 5 | 15.35 | 155 | 0.52 | 44 |
| 14(**) | 1.31 | " | 15 | 21.35 | 210 | 0.5 | 56 |
| 15 | 1.33 | KOAc | 50 | 18.75 | 150 | 0.27 | 83 |
| 16 | 0.22 | LiOAc | 50 | 5.25 | 40 | 0.21 | 29 |

*Example carried out on 1,253 mmols of methyl acetate and without introducing acetic acid into the inital charge.
**The duration of the experiment was 1 hour.

EXAMPLES 17 to 20

Using the autoclave and the procedure described above, a series of experiments was carried out with a charge consisting of 75 ml of methyl acetate, 20 ml of acetic acid, 5 ml of water, 18 mmols of methyl iodide, 0.22 mmol of cobalt acetate tetrahydrate, 1.31 mg atoms of ruthenium in the form of triruthenium dodecacarbonyl, and sodium acetate, of which the amount introduced is reported in Table V below.

The common operating conditions were as follows:
$H_2/CO$ 2/1 (molar ratio)
Temperature : 215° C.
Total pressure at the temperature indicated : 260 bars
Duration of the experiment at the temperature indicated : 40 Minutes.

The particular conditions and also the results obtained are also reported in Table V below.

Control experiment f was carried out in the absence of sodium acetate.

TABLE V

| Example No. | AcONa mmols | AcOEt (g) | MeOH (g) | AcH (g) | EtOH (g) | AcOH (g) |
|---|---|---|---|---|---|---|
| 17 | 10 | 4.93 | 2.56 | 1.14 | 1.17 | 33.9 |
| 18 | 20 | 9.84 | 2.39 | 0.34 | 1.72 | 32.5 |
| 19 | 35 | 8.27 | 2.03 | 0.06 | 1.26 | 32.7 |

TABLE V-continued

| Example No. | AcONa mmols | AcOEt (g) | MeOH (g) | AcH (g) | EtOH (g) | AcOH (g) |
|---|---|---|---|---|---|---|
| 20 | 50 | 5.90 | 1.58 | | 0.64 | 30.6 |
| f | 0 | 2.86 | 2.64 | | 0.60 | 30.4 |

EXAMPLES 21 to 23

Using the autoclave and the procedure described above, a series of experiments was carried out with a charge consisting of 75 ml of methyl acetate, 20 ml of acetic acid, 5 ml of water, 18 mmols of methyl iodide, 0.2 mmol of cobalt acetate tetrahydrate 1.31 mg atoms of ruthenium in the form of triruthenium dodecacarbonyl, and lithium acetate, of which the amount introduced is shown in Table VI below.

The common operating conditions were as follows:
$H_2CO$ : 2/1 (molar ratio)
Temperature : 215° C.
Total pressure at the temperature indicated : 260 bars
Duration of the experiment at the temperature indicated : 40 minutes.

The particular conditions and also the results obtained are also reported in Table VI below.

Control experiment f was carried out in the absence of lithium acetate.

TABLE VI

| Example No. | AcOLi mmols | AcOEt (g) | MeOH (g) | AcH (g) | EtOH (g) | AcOH (g) | Productivity |
|---|---|---|---|---|---|---|---|
| 21 | 10 | 5.45 | 2.51 | 0.67 | 1.73 | 32.7 | 160 |
| 22 | 25 | 10.7 | 2.18 | 0.57 | 2.20 | 37.3 | 300 |
| 23 | 40 | 9.26 | 2.12 | 0.40 | 2.08 | 38.6 | 280 |
| f | 0 | 2.86 | 2.64 | — | 0.60 | 30.4 | 57 |

EXAMPLE 24

Using the equipment and the procedure described above, an experiment was carried out with a charge consisting of 77 ml of methyl acetate, 20 ml of acetic acid, 3 ml of water, 35 mmols of methyl iodide, 0.22 mmol of cobalt acetate hydrate, 1.31 mg atoms of ruthenium in the form of triruthenium dodecacarbonyl and 17 mmols of lithium acetate. After a reaction time of 40 minutes at 215° C., under a total pressure maintained at 250 bars by introducing additional amounts of a mixture of $H_2/CO=2/1$ (molar ratio), the following were determined:
AcOEt = 7.37 g (productivity = 220 g/hour x liter)
MeOH = 2.92 g
AcH = 0.90 g
EtOH = 1.79 g
AcOH = 34.5 g

EXAMPLE 25

Example 24 above was repeated, only the volume of methyl acetate introduced (80 ml) and the amount of methyl iodide (30 mmols) being modified.
The results obtained were as follows:
AcOEt = 8.71 g (productivity = 260 g/hour x liter)
MeOH = 1.88 g
AcH = 0.58 g
EtOH = 1.80 g
AcOH = 33.2 g

EXAMPLE 26

Example 25 above was repeated, the lithium acetate being replaced by 30 mmols of sodium acetate.
The results obtained were as follows:
AcOEt = 11.7 g (productivity = 350 g/hour x liter)
MeOH = 2.57 g
AcH = 1.02 g
EtOH = 1.62 g
AcOH = 35.6 g

EXAMPLE 27

Example 25 was repeated, the lithium acetate being replaced by 17 mmols of magnesium acetate tetrahydrate.
The results were as follows:
AcOEt = 8.50 g (productivity = 260 g/hour x liter)
MeOH = 1.72 g
AcH = 1.18 g
EtOH = 1.05 g
AcOH = 35.1 g

EXAMPLE 28

Using the autoclave and the procedure described above, a mixture of hydrogen and carbon monoxide, in the (molar) ratio 1, was reacted with a charge consisting of 80 ml of methyl acetate, 20 ml of acetic acid, 3 ml of water, 0.22 mmol of cobalt iodide, 1.31 mg atoms of ruthenium in the form of triruthenium dodecacarbonyl, and 30 mmols of sodium iodide.

After a reaction time of 20 minutes at 215° C., the total pressure then being 250 bars, the following were determined
AcOEt = 6.88 g (productivity = 210 g/hour x liter)
MeOH = 2.41 g
AcH = 0.49 g
EtOH = 2.08 g
AcOH = 35.3 g

EXAMPLE 29

Using the autoclave and the procedure described above, a mixture of hydrogen and carbon monoxide, in the (molar) ratio 2/1, was reacted with a charge consisting of 76 ml of methyl acetate, 20 ml of acetic acid, 3 ml of water, 0.22 mmol of cobalt acetate tetrahydrate, 1.31 mg atoms of ruthenium in the form of triruthenium dodecacarbonyl, 15 mmols of lithium iodide and 15 mmols of methyltriphenylphosphonium iodide.

After a reaction time of 20 minutes at 215° C., the total pressure then being 250 bars, the following were determined:
AcOEt = 7.79 g (productivity = 230 g/hour x liter)
MeOH = 1.97 g
AcH = 2.77 g
EtOH = 1.09 g
AcOH = 39.6 g
$CH_3I$ = 650 mg

EXAMPLE 30

Using the autoclave and the procedure described above, a mixture of hydrogen and carbon monoxide, in the (molar) ratio 2/1, was reacted with a charge consisting of 80 ml of methyl acetate, 20 ml of acetic acid, 3 ml of water, 0.22 mmol of cobalt acetate tetrahydrate, 1.31 mg atoms of ruthenium in the form of triruthenium dodecacarbonyl, 30 mmols of sodium iodide and 17 mmols of magnesium acetate tetrahydrate.

After a reaction time of 20 minutes at 215° C., the total pressure then being 250 bars, the following were determined:

AcOEt = 8.39 g (productivity = 250 g/hour x liter)
MeOH = 1.99 g
AcH = 0.99 g
EtOH = 2.08 g
AcOH = 37.4 g
$CH_3I$ = 370 mg While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an alkyl carboxylate, comprising hydrocarbonylating the next lower homolog thereof, wherein said next lower homolog has the formula R—CO—OR', in which R represents a linear or branched chain alkyl radical having from 1 to 16 carbon atoms, a cycloalkyl radical having from 3 to 6 carbon atoms, a phenyl radical ($C_6H_5$—), a radical $C_6H_5$—$C_xH_{2x}$— or a radical $C_xH_{2x+1}$—$C_6H_4$—, x being an integer between 1 and 6 inclusive, and R' is methyl, by reacting said next lower homolog with a gaseous mixture containing carbon monoxide and hydrogen in the simultaneous presence, in the reaction medium, of a catalytically effective amount of ruthenium, cobalt, the atomic ratio Co/Ru being in the range of from about 0.01 to 1, lithium acetate, at least one alkyl iodide and at least one inorganic or organic ionic iodide in which the cation is an alkali metal cation, alkaline earth metal cation, or phosphonium cation, the total amount of iodine-containing promoters present in the reaction medium being such that the atomic ratio I/Ru is greater than or equal to 5.

2. The process as defined by claim 1, wherein R is an alkyl radical having at most 4 carbon atoms.

3. The process as defined by claim 1, wherein the amount of ruthenium is between 0.5 and 100 mg atoms per liter of reaction medium.

4. The process as defined by claim 1, wherein the alkyl iodide has the formula R"I, in which R" represents a linear or branched chain alkyl radical having from 1 to 5 carbon atoms.

5. The process as defined by claim 4, wherein R" is an alkyl radical having from 1 to 4 carbon atoms.

6. The process as defined by claim 1, wherein the cation of the ionic iodide is an alkali metal cation.

7. The process as defined by claim 1, wherein the cation of the ionic iodide is a phosphonium cation having the formula I to III:

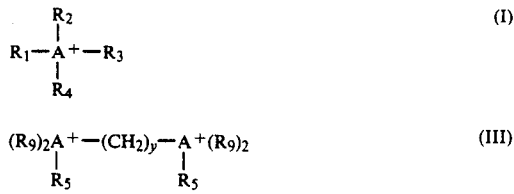

in which A is a phosphorus atom and $R_1$, $R_2$, $R_3$ and $R_4$, which may be the same or different, are hydrogen or organic radicals with the free valencies thereof borne by a carbon atom, and wherein any two of said radicals may together form a single divalent radical; $R_5$ is an alkyl radical having from 1 to 4 carbon atoms, and $R_9$, which can be identical to $R_5$, is an alkyl radical having from 1 to 4 carbon atoms, or a phenyl radical, and y is an integer between 1 and 10, inclusive.

8. The process as defined by claim 7, wherein the cation of the ionic iodide is a cation of the formula (I) in which $R_1$ to $R_4$ represent linear or branched chain alkyl radicals or monocyclic cycloalkyl, aralkyl or aryl radicals having at most 16 carbon atoms, further wherein said radicals may be substituted by 1 to 3 alkyl radicals, having from 1 to 4 carbon atoms, and two of the radicals $R_1$ to $R_4$ may together form a single divalent alkylene or alkenylene radical containing 3 to 6 carbon atoms and comprise 1 or 2 ethylenic double bonds, and further wherein said radical may be substituted with 1 to 3 alkyl substituents having from 1 to 4 carbon atoms.

9. The process as defined by claim 7, wherein any one of the radicals $R_1$ to $R_4$ is a linear alkyl radical having from 1 to 4 carbon atoms.

10. The process as defined by claim 7, wherein the cation of the ionic iodide is a quaternary phosphonium cation of the formula (I) in which any one of the radicals $R_1$ to $R_4$ is a linear alkyl radical having from 1 to 4 carbon atoms, the other three radicals being identical and being phenyl, tolyl or xylyl radicals.

11. The process as defined by claim 1, wherein the amount of ionic iodide introduced is such that the ratio $I^-$/Ru is between 1 and 100.

12. The process as defined by claim 1, wherein the total amount of iodine-containing promoters present in the reaction medium is such that the atomic ratio I/Ru is between 10 and 50.

13. The process as defined by claim 1, wherein methyl iodide, a quaternary phosphonium iodide and lithium acetate are present at the beginning of the reaction.

14. The process as defined by claim 1, wherein methyl iodide is the alkyl iodide and the molar ratio $CH_3I$/Ru is greater than or equal to 5.

15. The process as defined by claim 1, which is carried out in the liquid phase.

16. The process as defined by claim 1, wherein the reaction is conducted at a temperature ranging from 175° to 250° C.

17. The process as defined by claim 16, wherein the reaction is carried out under a total pressure ranging from 50 to 600 bars.

18. The process as defined by claim 17, wherein the molar ratio $H_2$/CO ranges from 1/5 to 5/1.

* * * * *